United States Patent [19]

Nilsson

[11] 4,280,647
[45] Jul. 28, 1981

[54] SLIT VALVE VENTILATOR AND METHOD OF ATTACHING SAME

[75] Inventor: Gösta Nilsson, Gemla, Sweden

[73] Assignee: AB Gemla Plast, Sweden

[21] Appl. No.: 111,891

[22] Filed: Jan. 14, 1980

Related U.S. Application Data

[63] Continuation-in-part of Ser. No. 924,652, Jul. 14, 1978, abandoned.

[51] Int. Cl.³ .............................................. B25C 7/00
[52] U.S. Cl. ................................. 227/147; 98/41 AV; 29/432.1; 227/156
[58] Field of Search ......... 29/432.1; 98/41 R, 41 AV; 227/83, 147, 156, 152; 403/379

[56] References Cited

U.S. PATENT DOCUMENTS

| | | | |
|---|---|---|---|
| 231,979 | 9/1880 | Ball | 29/432.1 |
| 2,341,113 | 2/1944 | Nelson | 98/41 R |
| 2,369,303 | 2/1945 | Kurth et al. | 98/41 R |
| 2,672,087 | 3/1954 | Marr | 98/41 R |
| 3,299,797 | 1/1967 | Day | 98/41 R |
| 3,308,745 | 3/1967 | Davies | 98/41 R |
| 3,640,557 | 2/1972 | Nute, Jr. et al. | 403/379 |
| 3,945,414 | 3/1976 | Gordon | 227/83 X |
| 4,138,779 | 2/1979 | Weber | 29/432.1 |

FOREIGN PATENT DOCUMENTS

| | | | |
|---|---|---|---|
| 523672 | 7/1940 | United Kingdom | 98/41 R |
| 617037 | 1/1949 | United Kingdom | 98/41 AV |

Primary Examiner—Paul A. Bell
Attorney, Agent, or Firm—Klarquist, Sparkman, Campbell, Leigh, Whinston & Dellett

[57] ABSTRACT

An air supply means includes a frame providing a valve seat and defining a valve opening. A valve body is adjustably connected to the frame. A plurality of V-shaped fasteners are used to secure the frame in an air duct. Each fastener has a pair of angularly disposed legs receivable in a slot in the opposed top and bottom walls of the frame, the legs meeting at an apex which is positioned toward the entrance to the duct. To attach the frame to the duct, a punch-like member is used to strike the apex of the fastener to spread the legs thereof and drive them through the slots in the opposing walls of the frame and thence, into the walls of the duct.

3 Claims, 7 Drawing Figures

SLIT VALVE VENTILATOR AND METHOD OF ATTACHING SAME

CROSS-REFERENCE TO RELATED APPLICATION

This application is a continuation-in-part of my presently co-pending application Ser. No. 924,652, filed July 14, 1978, and now abandoned.

BACKGROUND OF THE INVENTION

This invention relates to an air supply means for use in conjunction with air-tight windows and, more particularly, to a slit valve ventilator for use as a window valve.

Ventilators of this type generally comprise a frame adapted to be mounted in the entrance to a slot-like air duct, the frame providing a valve seat and defining a valve opening, and a valve body adjustably connected to the frame for closing the valve opening. Valves of this type, generally arranged under a window sill, were widely used about 40 years ago, but subsequently fell into disfavor due to poor functioning, leaking and heat conduction.

In order to conserve energy today, it is highly desirable to make windows extremely air-tight. Because of this building standards have been promulgated to require that each room be provided with a fresh air ventilator having a ventilation area of at least 30 cm$^2$. The ventilator must also be adjustable and absolutely air-tight when closed. In most cases a slit valve type of ventilator installed either above or below the sash will be chosen to meet these requirements. However, presently available devices are generally unsatisfactory for the reasons above set forth.

It is thus the object of the present invention to provide a window ventilator of the slit valve type which is air-tight when closed and easy to install and operate.

It is a further object of the present invention to provide a means and method of attaching a ventilator of the above type to an air duct which will render installation quick and easy and which will achieve a tight fit.

SUMMARY OF THE INVENTION

The air supply means of the present invention comprises a frame adapted to be mounted in the entrance to a slot-like air duct, the frame providing a valve seat and defining a valve opening, and a valve body adjustably connected to the frame. At least one V-shaped fastener is provided, the fastener extending between the opposing walls of the frame, for attaching the frame to the air duct, the fastener having a pair of angularly disposed legs meeting at an apex, each leg of the fastener being received in a slot disposed in an opposing wall in the frame, the apex of the fastener being directed toward the valve opening for subjection, on mounting the frame in the duct, to a force which spreads the legs of the fastener and drives them through the slots and into the walls of the air duct.

The invention further provides a method of mounting a frame in the entrance to a slot-like duct having parallel top and bottom walls. The method comprises providing a slot in each of the opposing top and bottom walls of the frame, positioning a fastener in the frame, the fastener having a pair of legs joined at an apex to form a generally V-shaped body, the fastener being positioned in the frame whereby the apex is disposed toward the entrance to the duct, the legs being disposed one in each of the slots in the opposing walls of the frame, and striking the fastener on the apex thereof to spread the legs and drive them through the slots and into the walls of the duct, the fastener being driven inwardly of the frame to a point wherein the apex is not disposed forwardly of the slots, the legs penetrating the walls of the duct to retain the frame snugly therein.

DESCRIPTION OF THE PREFERRED EMBODIMENTS

Figure 1:
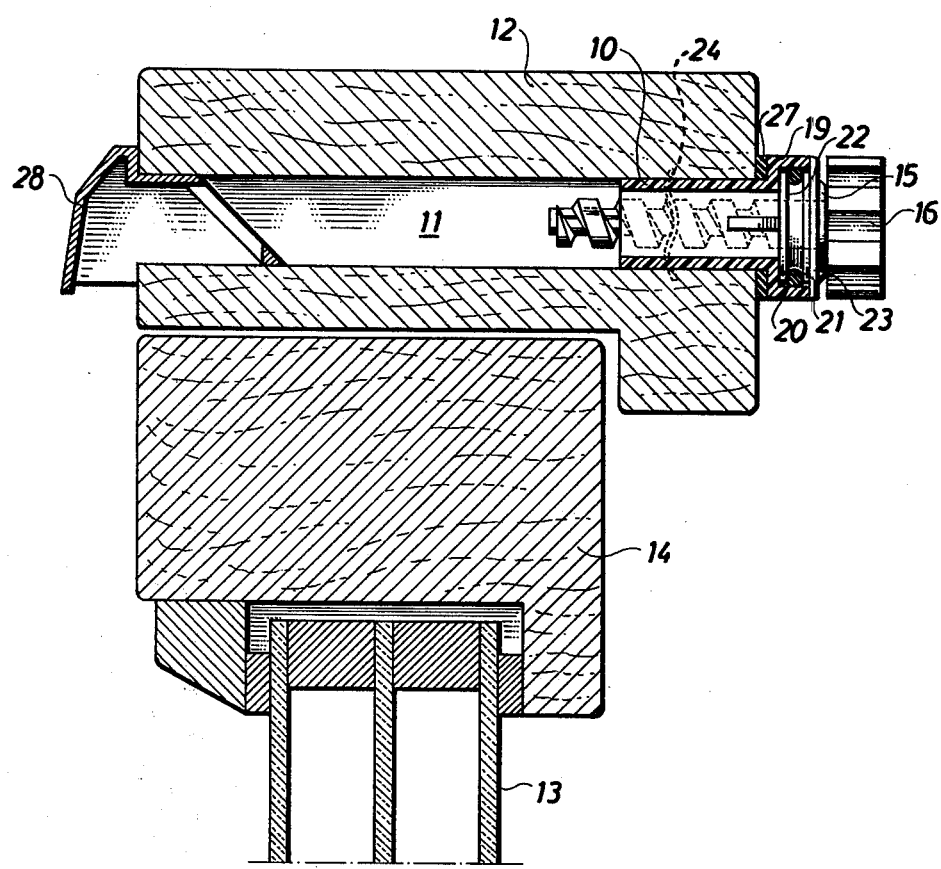
FIG. 1 is a cross-sectional view through the upper part of a window provided with a ventilator in accordance with the present invention, the ventilator being illustrated in the closed position.
Figure 2:
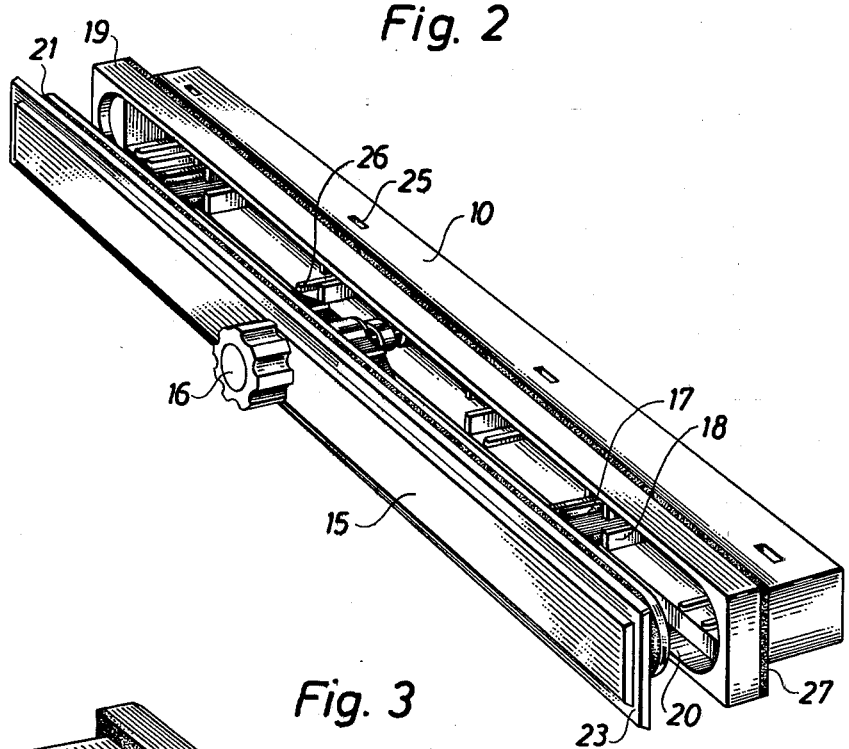
FIG. 2 is a perspective view of the ventilator in the open position.
Figure 3:
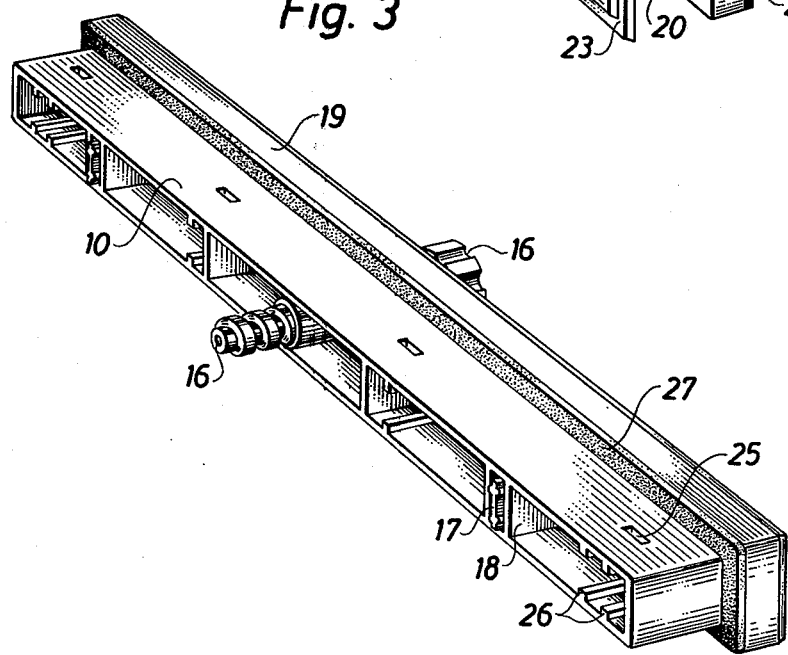
FIG. 3 is a perspective view of the ventilator in the closed position.

Referring to the drawings, the ventilator of the present invention includes a frame 10 adapted to be mounted in a slot-like air duct 11, the duct being illustrated above a frame head 12 of a window provided with triple glazing 13 in a sash 14

A valve body 15 is provided for opening and closing the ventilator, the valve body 15 being movable in a direction perpendicular to the plane of the valve opening provided by the frame 10. In order to accomplish this purpose, an adjusting screw 16 is rotatably mounted in the valve body 15 in threaded engagement with the frame 10. A pair of guide tongues 17 movable in guides 18 in the frame 10 are also provided.

The frame 10 is further provided with a collar 19 having inwardly disposed, axially directed surfaces which form a valve seat 20. The collar 19 provides an abutment surface 33 at the opening of the frame 10 for a purpose hereinafter to be described.

An O-ring 21 on the valve body 15 is provided to coact with the valve seat 20. The O-ring 21 is positioned in a groove 22 which extends around the rectangular periphery of the valve body 15, the groove 22 being located on the valve body at a position slightly inside the aperture formed in the collar 19. A shoulder 23 defines the closing position of the valve body 15 for coaction with the edge of the collar 19.

Figure 4:
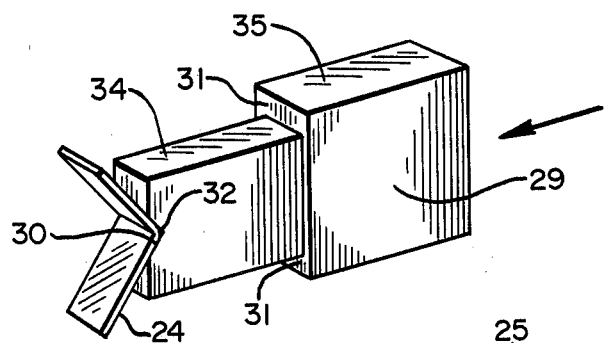
FIG. 4 is a perspective view of a V-shaped fastener suitable for use in the present invention together with a tool for use in installing the ventilator, the tool and the fastener being illustrated in operative relation.
Figure 5:
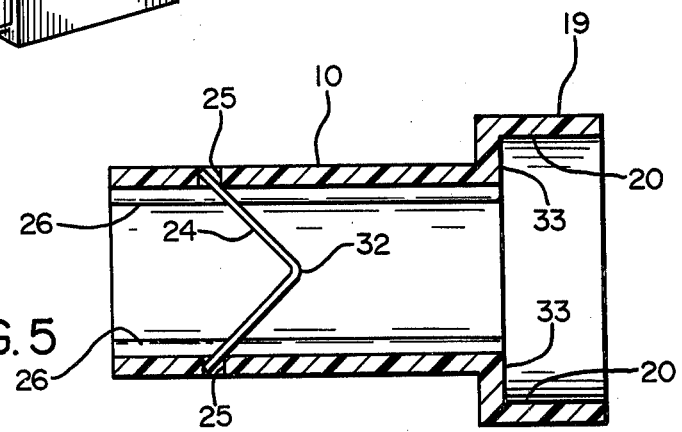
FIG. 5 is a sectional view of the frame with the V-shaped fastener in position therein.

The frame 10 is installed and secured in the air duct 11 by means of a plurality of metal fasteners 24, which fasteners are V-shaped in their initial (disengaged) state. See FIG. 4. Each of the fasteners 24 has a pair of angularly disposed legs which meet at an apex 32. The fasteners are positioned in the frame such that each leg of a fastener is received in a slot 25 in the opposed top and bottom walls of the frame. The apex 32 is directed outwardly toward the valve opening as shown in FIG. 5. At this time the fasteners 24 are retained laterally and guided by ribs 26.

Figure 6:
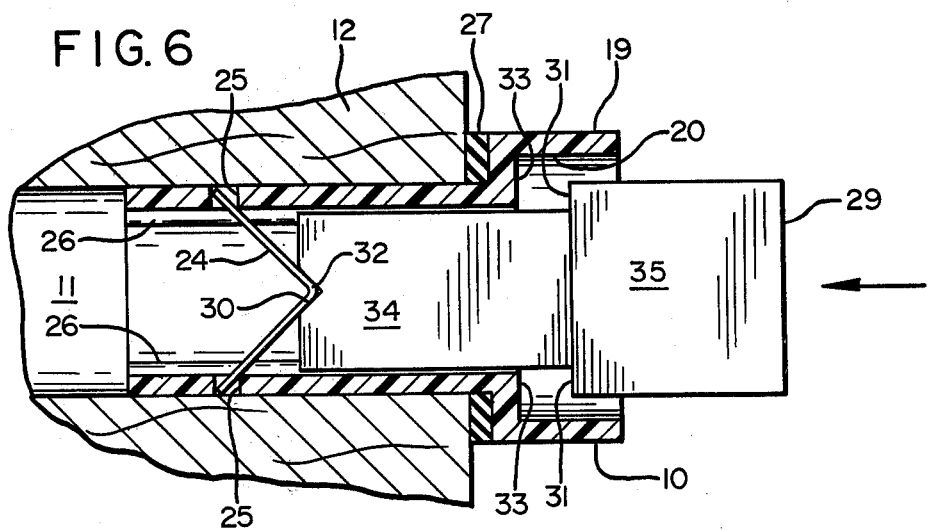
FIG. 6 is a sectional view of the frame inserted in the duct with the tool in initial contact with the apex of the fastener.
Figure 7:
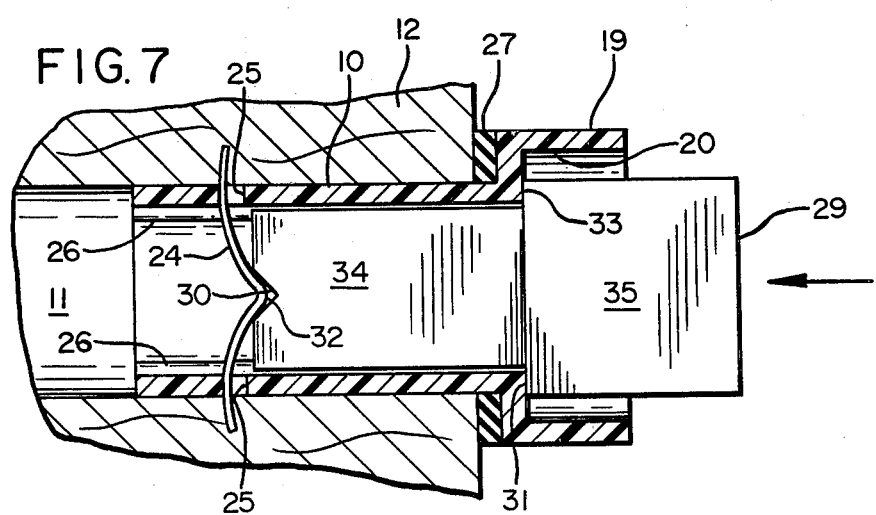
FIG. 7 is a cross-sectional view similar to FIG. 6 illustrating the tool bottomed on the shoulder of the frame after it has driven the legs of the fastener through the slots in the frame walls and into the walls of the duct.

To install the ventilator in the air duct 11, the frame 10 is first pressed into the duct. A punch 29 having an enlarged head 35 adapted to fit within the opening of the collar 19, and a punching portion 34 having a V-shaped recess 30 centrally disposed in its operative end, is inserted in the opening of the collar 19 with the recess 30 in engagement with the apex 32 of the fastener 24. See FIGS. 4 and 6. The enlarged head 35 provides an annular shoulder 31 which can bottom on the abutment surface 33 of the collar 19. When the punch 29 is struck, as by a hammer, the fastener 24 is driven forwardly such that its legs are spread and thrust outwardly through the slots 25 and into the walls of the duct. The fastener legs ride on and come to rest in contact with the forward edges of the slots 25, snugly to retain the frame 10 within the duct 11. See FIG. 7.

The shoulder 31 of the punch 29 bottoms on the abutment surface 33 of the collar 19 (see FIG. 7) and since the punching portion 34 extends no further inwardly than the location of the slots 25, the shoulder 31 prevents the punch from driving the fasteners in too far, which might otherwise cause them to be given a reverse V-shape and possibly, be driven out of contact with the duct walls.

A seal 27 is disposed between the inwardly disposed shoulder of collar 19 and the exterior edge of the air duct. It is also preferable to install a rain guard 28 over the inlet aperture of the duct. See FIG. 1.

I claim:

1. In combination, a generally solid body having a slot-like duct disposed therein;
   a frame having opposed parallel top and bottom walls, said frame being insertable in said duct, said frame having an exterior collar fitting around the entrance to said duct, said frame having at least one slot in each opposed top and bottom walls thereof;
   at least one generally V-shaped fastener having a pair of angularly disposed legs meeting at an apex, said legs being disposed one in each of said slots in said opposed top and bottom walls of said frame, said apex being disposed toward said entrance to said duct; and
   a punch-like installing tool having an enlarged head and a punching portion centrally disposed thereon, said tool being inserted in said frame with said punching portion in engagement with the apex of said fastener, said head being adapted to contact said exterior collar of said frame and bottom thereupon, said center portion extending no further inwardly of said frame than the location of said slots in said walls of said frame when said head bottoms on said collar,
   whereby striking said head of said tool spreads the legs of said fastener and drives them through said slots into the walls of said duct, said apex of said fastener being driven within said frame to a point which is not forward of said slots.

2. The combination of claim 1 in which said punching portion of said tool is provided with a V-shaped recess in the forwardly disposed end thereof, said recess being adapted to engage said apex of said fastener.

3. The combination of claim 1 in which said frame is provided with guide means on said top and bottom walls thereof laterally to retain said fastener.

* * * * *